United States Patent [19]

Shaw et al.

[11] Patent Number: 4,790,991
[45] Date of Patent: Dec. 13, 1988

[54] INGESTIBLE AGGREGATE AND DELIVERY SYSTEM PREPARED THEREFROM

[75] Inventors: James J. Shaw, Morristown; Shri C. Sharma, Mendham, both of N.J.

[73] Assignee: Warner-Lambert Company, Morris Plains, N.J.

[21] Appl. No.: 161,541

[22] Filed: Feb. 29, 1988

Related U.S. Application Data

[62] Division of Ser. No. 698,511, Feb. 5, 1985, Pat. No. 4,747,881.

[51] Int. Cl.$^4$ .......................... A23C 1/29; A61K 9/16
[52] U.S. Cl. .................................... 424/441; 514/819; 514/838; 514/824; 426/2; 426/74
[58] Field of Search .................... 514/819, 838, 824; 424/441; 426/2, 74

[56] References Cited

U.S. PATENT DOCUMENTS

| | | | |
|---|---|---|---|
| 2,441,927 | 5/1948 | Adams | 106/209 |
| 2,444,412 | 7/1948 | Swanson | 106/209 |
| 3,308,020 | 3/1967 | Wolf et al. | 424/78 |
| 3,383,281 | 5/1968 | Wolf et al. | 424/78 |
| 3,499,960 | 3/1970 | Macek et al. | 514/974 |
| 3,780,171 | 12/1973 | Irrascher et al. | 424/79 |
| 3,821,414 | 6/1974 | Monti | 514/780 |
| 3,827,899 | 8/1974 | Zirlin | 106/209 |
| 3,843,819 | 10/1974 | Rostagno | 426/363 |
| 3,907,983 | 9/1975 | Seth | 514/951 |
| 3,914,456 | 10/1975 | Norsby | 426/579 |
| 3,959,472 | 5/1976 | Cannalonga et al. | 514/951 |
| 3,970,750 | 7/1976 | Brockemeyer et al. | 424/153 |
| 3,974,272 | 8/1976 | Polli et al. | 424/78 |
| 4,041,153 | 8/1977 | Howard | 424/131 |
| 4,064,234 | 12/1977 | Howard | 424/157 |
| 4,140,756 | 2/1979 | Gallian | 424/475 |

(List continued on next page.)

FOREIGN PATENT DOCUMENTS

| | | |
|---|---|---|
| 2629773 | 1/1978 | Fed. Rep. of Germany . |
| 7932 | 5/1970 | France . |
| 58-39608 | 3/1983 | Japan . |
| 59-187744 | 10/1984 | Japan . |
| WO80/00658 | 4/1980 | PCT Int'l Appl. . |
| 490001 | 8/1938 | United Kingdom . |
| 929391 | 6/1963 | United Kingdom . |
| 1132233 | 10/1968 | United Kingdom . |
| 1181003 | 2/1970 | United Kingdom . |
| 1262556 | 2/1972 | United Kingdom . |
| 1446352 | 8/1976 | United Kingdom . |
| 1573487 | 8/1980 | United Kingdom . |
| 2050828A | 1/1981 | United Kingdom . |

OTHER PUBLICATIONS

Arnold, J., et al., "Bioavailability and Pharmacokinetics of a New Slow-Release Potassium Chloride Capsule", J. Pharm. Sci., 1980, 69/12, pp. 1416–1418.

Costa, F. V., et al., "Efficacy and Tolerability of a New Microencapsulated Potassium Chloride in Hypertensive Patients", Curr. Thera. Res., 1983, 33/611, pp. 1112–1119.

Primary Examiner—Ronald W. Griffin
Attorney, Agent, or Firm—Daniel A. Scola, Jr.; Sandra Gusciora Field

[57] ABSTRACT

The present invention relates to an ingestible aggregate comprising a pre-swelled substantially anhydrous hydrocolloid and a substrate. More particularly this invention relates to an aggregate having as a substrate a dietary fiber and/or drug wherein the composition can be administered in a therapeutically effective amount. Hydrocolloids useful include natural and modified gums, celluloses, modified celluloses, pectins, mucillages, modified starches, noncellulose polysaccharides, algal polysaccharides and mixtures thereof. The aggregate should be in the size range of about 4 to about 70 U.S. mesh. The unpleasant taste and mouthfeel of the fiber and/or drug is effectively masked and substantial hydration is delayed until the compositions reaches the stomach. The compositions are substantially more palatable, devoid of graininess, bitterness or fibrous texture. The pleasant taste of the composition encourages patient compliance with their fiber or drug therapy.

9 Claims, 2 Drawing Sheets

INGESTIBLE AGGREGATE AND DELIVERY SYSTEM PREPARED THEREFROM

This is a divisional of copending application Ser. No. 698,511 filed on Feb. 5, 1985 now U.S. Pat. No. 4,747,881, issued May 31, 1988.

FIELD OF THE INVENTION

The present invention relates to an ingestible aggregate comprising a pre-swelled substantially anhydrous hydrocolloid and a substrate. More particularly this invention relates to a composition having as a substrate a dietary fiber and/or drug wherein the composition can be administered in a therapeutically effective amount. The unpleasant taste and mouthfeel of the fiber and/or drug is effectively masked and substantial hydration is delayed until the composition passes through the oral cavity. The compositions are substantially more palatable, devoid of graininess, bitterness or fibrous texture. The pleasant taste of the composition encourages patient compliance with a recommended therapy.

BACKGROUND OF THE INVENTION

Prescribed daily dosage amounts for fiber are often very high, requiring the patient to administer the fiber or fiber composition several times per day. While their benefits are well known to the consuming public, the unpleasant fibrous mouthfeel and texture of products containing dietary fiber has resulted in reluctance of patients to comply with prescribed dosages.

Patient compliance with prescribed drug therapies is also a problem particularly when the drug has an unpleasant taste, after-taste or gritty mouthfeel. Drugs such as cholestryamine and potassium chloride are known to taste unpleasant. The prior art has disclosed products to mask the taste of these drugs, but the products themselves often suffer from their own unpleasant tastes. The trend, therefore, in patient use of the prior art products containing fiber or drugs has been to deviate from the prescribed dosage or frequency of dosage, thereby diminishing the effectiveness of the therapy.

Two patents which disclose palatable drug formulations use coacervation techniques to combine cholestyramine with modified celluloses. U.S. Pat. No. 3,974,272 shows oral palatable formulations containing aqueoue media and cholestyramine. A method of treating hypercholestrolemia is claimed. Chewable products containing cellulosic/gum colloids are disclosed.

U.K. Pat. No. 1,446,352 concerns palatable compositions useful for the treatment of hypercholesterolemia and biliary cirrhosis. The invention provides a liquid composition containing "coacervate of cholestyramin with a cellulose hydrocolloid" derivative. By the term "coacervate" is meant the coagulation of two hydrophilic substances of opposite charge. Representative hydrocolloids are methyl and ethyl cellulose, sodium carboxymethyl cellulose, hydroxyethyl cellulose and hydroxypropyl cellulose. A water-insoluble dispersing agent, e.g., a substituted carboxymethyl-starch, is optional. In making the composition, 1 part by weight of hydrocolloid is combined with 4 to 10 parts of cholestyramine by dry mixing and passing through a No. 80 U.S. standard mesh screen. The resulting powder is then mixed with a liquid to form a coacervate which can be orally administered.

With respect to dietary fiber, numerous attempts to mask the fibrous mouthfeel have been tried. Various baked products, granola-type products, cereals and snack-food products have attempted to incorporate fiber in confectionery systems. These products are generally high in caloric value and relatively low in dietary fiber. The objective of the prior art has been to attempt to conceal the unpleasant taste and texture of the fiber by using various materials such as fats, polyhydric alcohols, sugar solids or starch. While the objective is achieved to some degree, these materials increase the caloric value and dilute the effective dose. High amounts of fiber, e.g., amounts greater than about 5%, typically were dry-tasting with an unpleasant fibrous mouthfeel.

Fiber products which are specifically intended for bowel normalization and related disorders include those which are slurried in water. With respect to the prior art attempts to make a fiber product which is added to water and drunk as a slurry, the fiber tended to clump together, forming slimy, unpalatable masses. These fiber clumps were comprised of hydrated hydrocolloids, e.g., pysillium. High amounts of excipients were necessary to minimize clumps. These excipients or dispersing aids were generally carbohydrate or fat materials such as sugar, dextrose and the like, which are high in caloric value.

Conventionally, fiber is incorporated into edible substances as fine powder. There are several reasons for this. Fine powdered fiber is less apt to form "fish-eye" clumps when hydrated, e.g., clumps having a dry center and wet surface. Furthermore, the purification of fiber often involves steps which reduce the particle size of fiber. Few soluble dietary fibers, with the exception of guar gum, hydrate sufficiently or uniformly unless the particle size is fine. Fine particles are, however, difficult to handle and process and product containing above 10 to 15% dietary fiber have unpalatable and fibrous textures.

It is well known that the functionality and effectiveness of fiber and certain drugs such as ion exchange resins is dependent on the active surface area. Fine particles achieve the desired therapeutic effects more effectively than course particles because the former have a higher surface area to weight ratio, e.g., a higher active surface. For example, in the case of ion exchange resins, e.g., cholestyramine, a greater surface area allows enhanced adsorption of bile acids, increased ion exchange, as well as other surface phenomena. In the case of fiber, increased surface area allows for increased adsorption of, and combination with, liquids, body metabolites and the like. The result is increased bulk and swelling upon adsorption which is therapeutically desirable.

While coarse substrate particles do not have sufficient effective surface area to be as effective as the finer particles, finer particles also suffer from certain handling, processing, and formulation problems. The finer particles, having a larger total surface area than coarser particles, tend to be organoleptically perceived as too dry or dusty, and in the case of certain fibers a pasty taste results. These organoleptic characteristics are undesirable. Additionally, when fine particles are added in therapeutic amounts to a delivery matrix, e.g., a confectionery formulation, the fine particles tend to disrupt the continuous phase characteristics of the final product.

It has been discovered that these and other problems associated with coarse as well as fine substrate particles of fiber or drugs can be remedied by formation of an aggregate comprising a substantially anhydrous preswelled hydrocolloid and a substrate, which aggregate has a particle size of about 4 to about 70 standard U.S. mesh. Outside these ranges, some or all of the disadvantages discussed above become apparent.

SUMMARY OF THE INVENTION

This invention relates to an ingestible substantially anhydrous aggregate comprising a pre-swelled hydrocolloid and a solid substrate, wherein the hydrocolloid at least partially entraps and binds the substrate, the substrate being selected from the group consisting of dietary fibers, drugs and mixtures thereof. This invention also relates to a method of optimizing the surface to weight ratio of substrate materials, such as drugs and dietary fiber, where these parameters are critical to the therapeutic efficacy of the substrate.

An alternative embodiment of the invention relates to a delivery system containing the ingestible aggregates as well as methods for treating various disorders such as cholesterolemia, mineral and vitamin deficiencies, colonic diseases, arrhythmia and related disorders.

DETAILED DESCRIPTION OF THE INVENTION

The inventive aggregates delay substantial hydration of the solid substrate until the substrate passes the oral cavity. One or more substrates is aggregated with a pre-swelled hydrocolloid material which at least partially entraps and binds the substrate particles together. The hydrocolloid and the substrate are not the same material. For example, if the substrate is dietary fiber, the fiber is protected against swelling until it reaches the stomach, at which time the dietary fiber becomes substantially hydrated, swelling to form a gel-like mass. Thus, the consumer can ingest and obtain the benefits of fiber without perceiving the fibrous taste. If the substrate is a drug, the coating serves to delay hydration of the drug in the same manner. The aggregate also serves to mask the unpleasant taste and textural attributes of the solid substrates.

The ratio of hydrocolloid material to the substrate depends to a large degree on the substrate chosen, as well as the choice of hydrocolloid. If the substrate is a drug, the hydrocolloid must delay hydration and mask any unpleasant taste and mouthfeel without affecting the efficacy of the drug. This is of a lesser concern when the substrate is dietary fiber. The ratio of hydrocolloid to substrate can therefore vary widely, but is preferably in the ranges of about 1:100 to about 1:5; about 1:200 to about 1:1: and about 3:1 to about 20:1.

The Substrate

The term "substrate" means the fiber or drug materials referred to herein which are combined with the hydrocolloid materials to form aggregates.

The term "solid" when used to describe the substrate includes particulate materials, crystalline materials, freeze-dried materials, wax-like materials and the like.

The term "ingestible" is meant to include all materials which are used by, or which perform a function in the body. Thus, materials which are not adsorbed or absorbed are included as well as non-digestible and digestible materials.

The term "pre-swelled" in connection with the hydrocolloid means the hydrocolloid was previously hydrated. In most cases, at least partial swelling due to hydration will occur.

For purposes of this invention, the term "fine" substrate particle indicates a standard U.S. mesh size number of greater than about 70. The term "coarse" substrate particle indicates a standard U.S. mesh size number of less than about 70.

The term "dietary fiber" is understood to mean the component of food which is non-digestible and non-metabolizable by humans. It is well known, however, that dietary fibers as they occur naturally in food sources also have associated with them a small digestible portion comprising fats, proteins and carbohydrates.

Dietary fiber can be divided into two broad categories: insoluble dietary fiber and water soluble dietary fiber. For purposes of this invention, "insoluble dietary fiber" means substantially non-swellable dietary fiber. "Soluble dietary fiber" means dietary fiber which is water soluble or water swellable. Soluble dietary fiber provides the bulking effect commonly associated with fiber.

The term "drug" when used to classify the substrate includes medicaments, vitamins, mineral supplements and other chemical or biological substances intended for use in the treatment, prevention, diagnosis, cure of mitigation of disease or illness, or substances which affect the structure or function of the body.

Useful dietary fiber substrates include non-cellulosic polysaccharides, pectin, gums, algal polysaccharides, cellulose, hemicellulose, lignin and mixtures thereof. The dietary fiber is present in the aggregate in amounts of about 25% to about 99.75% by weight; preferably in amounts of about 65 to about 85%; and most preferably about 68 to about 70%.

In the case of a fiber substrate, it is possible for the hydrocolloid and the substrate to be selected from the same class of materials. Preferably, however, the hydrocolloid and the fiber substrate ehould not be the identical material or species.

Suitable categories of drugs that may be employed in the instant aggregate may vary widely and generally represent any stable drug combination. Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamine maleate, doxylamine succinate, and phenyltoloxamine citrate;

(c) Decongestants, such as phenylephrine hydrochloride, phenylpropanolamine hydrochloride, pseudoephedrine, hydrochloride ephedrine;

(d) Various alkaloids, such as codeine phosphate, codeine sulfate and morphine;

(e) Mineral supplements such as potassium chloride and calcium carbonates, magnesium oxide and other alkali metal and alkaline earth metal salts;

(f) Laxatives, vitamins and antacids;

(g) Ion exchange resins such as cholestyramine;

(h) Anti-cholesterolemic and anti-lipid agents;

(i) Antiarrhythmics such as N-acetylprocainamide;

(j) Antipyretics and analgesics such as acetaminophen aspirin and ibuprofen;

(k) Appetite suppressants such as phenylpropanolamine hydrochloride or caffeine; and (l) Expectorants such as guaifenesin.

Additional useful active medicaments include anti-inflammatory substances, coronary dilators, cerebral dilators, peripheral vasodilators, anti-infectives, psychotropics, antimanics, stimulants, laxatives, decongestants, gastro-intestinal sedatives, antidiarrheal preparations, anti-anginal drugs, vasodialators, anti-arrythmics, antihypertensive drugs, vasoconstrictors and migrane treatments, antibiotics, tranquilizers, antipsychotics, antitumor drugs, anticoagulants and antithrombotic drugs, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, anti-uricemic drugs, and the like.

Mixtures of the druga and medicaments may also be used.

The preferred drugs are cholestyramine and potassium chloride. Cholestyramine is the chloride salt of a basic anion exchange resin which has an affinity for sodium chloride and a particularly strong affinity for acid materials such as bile acids. It occurs as a white powder, insoluble in water and has an amine-like odor and a gritty taste. Cholestyramine is believed to absorb and combine with bile acids in the intestine to form an insoluble complex which is then excreted by the body. Cholesterol is the major precusor of bile acids which are formed by the oxidation of cholesterol. The serum level of cholesterol can be reduced by administration of cholestyramine, which leads to reduction of bile acids and increased oxidation of cholesterol.

The racommended adult dosage of cholestyramine is about 5 to about 50 grams per day; preferably about 12 to about 32 grams per day. Administration is generally about 3 or 4 times daily in dosages of about 2 to 10 and preferably about 3 to 4 grams.

Potassium chloride is generally sold as a powder or tablet to be dissolved in cold water. Adult dosages are generally about 1.02 to about 2.56 grams (40-100 mEq) per day, administered in amounts of about 50 mEq about 1 or 2 times per day.

The drug is present in the aggreaate in amounts of about 50 to about 99% by weight; preferably about 65 to a bout 85%; and most preferably about 70 to about 80%.

The Hydrocolloid

Typically the hydrocolloid material is applied to the anhydrous substrate in the hydrated form via an aqueous solution. The hydrocolloid is sprayed onto the substrate and allowed to dry, as discussed hereafter. The hydrocolloid dries in what is believed to be the substantially uncoiled and open physical state. Upon re-hydration, e.g., in saliva, the hydrocolloid becomes slippery almost immediately. This slippery characteristic imparts lubricity to the particles to mask the physical texture of the substrate.

The hydrocolloid modifies the physical characteristics of the substrate. The hydrocolloid functions to some extent to entrap the substrate, but also binds fine particles of the substrate together into larger aggregates. At the higher concentrations of the hydrocolloid mentioned above, an increase in lubricity is imparted to the aggregate particles upon wetting, e.g., placement in water or in the mouth. The lubricity is primarily due to the slippery nature of the hydrated hydrocolloid surface. This characteristic is an advantage in that the mouthfeel perception of the consumer is that the particles are smooth and easy to swallow, being devoid of unpleasant texture or taste.

Useful hydrocolloids include natural and modified gums, celluloses and modified celluloses, pactin, mucillages, modified starched, noncellulosic polysaccharides, algal polysaccharides and mixtures thereof. Particularly preferred hydrocolloids include carboxymethyl cellulose, methyl cellulose, karaya gum, acacia gum, sodium alginate, calcium alginate, hydroxypropyl methyl cellulose and mixtures thereof.

The hydrocolloids are present in the aggregate, by weight of the aggregate, in amounts of about 0.25% to about 25%: preferably 0.5 to about 5%: and most preferably about 0.75 to about 3.0% by weight.

Preparation of the Aggregates

The process of preparing the aggregates comprises:
(a) preparing an aqueous composition of the hydrocolloid;
(b) contacting the substrate particles with the aqueous hydrocolloid composition to form the aggregates of the substrate and hydrocolloid, the aggregates having a particle size of about 4 to about 70 mesh; and
(c) drying and collecting the aggregates.

The preferred method of contacting the substrate with the hydrocolloid composition involves fluidized bed spray coating. The fluidizing and spraying may be carried out in a Uniglatt fluidized bed granulator or similar apparatus. The spray rate is preferably regulated at a pressure of about 1 to about 5 bar, and most preferably about 1.5 bar. One bar is equal to one dyne per centimeter or 750 mm of mercury. The flow rate should be regulated such that the particle size of the resultant aggregates is with the desired range. Preferably, spraying is interrupted by periods of air drying of the aggregates in the fluidized state. Spraying may be resumed one or more times to assure the aggregate particle size is sufficient.

Flavors, food grade acids, sweeteners, colors and other conventional additives may be optionally mixed with the final dried aggregates.

Delivery Systems Containing the Aggregates

The aggregates of the present invention may be incorporated in various delivery systems. Thus, this invention also contemplates a novel delivery system comprising:
(i) an edible matrix in amounts up to about 99% and preferably about 50 to about 85%;
(ii) an ingestible aggregate comprising a preswelled substantially anhydrous hydrocolloid and a substrate, wherein the hydrocolloid at least partially entraps and binds the substrate, the substrate being selected from the group consisting of dietary fiber, drugs and mixtures thereof, wherein the substrate and the hydrocolloid are not the identical material.

Component (ii) of the delivery system is substantially the same as previously described. various edible matrices may be used as component (i), such as confectionery, pharmaceutical preparations and the like. Confectionery matrices include the gel-type, candy bar type, boiled candy, chewable mint or tablet, nougat type or other candy forms. Pharmaceutical preparations include tablets, capsules, lozenges, gels, pellets, granules, powders and the like, and a wide variety of solid or semi-solid dosage forms which may be ingested with or without additional coating or binding agents.

Since taste masking is a key feature of the invention, the use of the invention in sublingual or buccal systems is contemplated, but not generally preferred. However, other systems in which the final product would not normally be expected to be retained in the mouth for significant amounts of time are contemplated. Thus, chewable and/or dissolvable dosage forms can be used.

One dosage form contemplated involves the use of gelatin or other plastic matrix(es) in a capsule containing the inventive aggregate and/or materials containing the inventive aggregate in combination with one or more conventional excipients.

By "excipients," Applicants mean substances and materials generally used in the drug or food industry which do not alter the character and function of the active component of the aggregate. Generally, preferred excipients include binders, sweeteners, colorants perfumes, processing aids, and the like. Mixtures of excipients are operable.

The most preferred matrix is a gel-type confectionery matrix which is particularly useful in that large amounts of the aggregate particles, e.g., about 10 to about 20% by weight of the confectionery product may be incorporated therein without unpleasant taste or texture.

The gel matrix is generally comprised of a gel-forming material, water, carbohydrate sweeteners and acidulents. Useful gel-forming materiale include pectin, gum arabic gels, starches, carrageenan gels, locust bean gum/xanathan gum gels, gelatin or glycerated gelatin gels and the like. Pectin is the preferred gel-forming material for the confectionery matrix.

In the instance where pectin is used as the gel-forming matrix the pH must be maintained within a specified range of about 3.2 to about 4.7 to insure adequate gellation. The pH is adjusted by the addition of acidulents and buffers. Acidulents may also impart taste and improve the flavor of the gel.

Preferably, the confectionery matrix is a gel-type matrix have the following formulation:

| Ingredient | % by weight of delivery system |
|---|---|
| Pectin | about 1.8 to about 5 |
| Water | about 40 to about 75 |
| Acidulent/buffer | up to about 5 |
| Sugar | about 10 to about 60 |
| Corn syrup solids | about 0 to about 50 |
| Aggregate locust bean gum/ carboxymethyl cellulose | about 4 to about 20 |
| Fruit | about 0 to about 10 (solids basis) |
| Glycerin | about 0 to about 20 |
| Gelatin | about 0 to about 10 |
| Flavor | about 0 to about 2 |

It should be mentioned that the water content of the final gel, about 15 to about 20%, is lower than the initial water content due to evaporation.

The gels are prepared by first combining the pectin with water to cause hydration. The pH is then adjusted to below about 4.5 by the addition of buffer, e.g., sodium citrate. Sugar and corn syrup is then added and mixed until dissolved. Up to this point, the process can be conducted at room temperature. The mixture is then boiled to obtain a desired solids content level, e.g., typically about 80 to about 90%, preferably about 81 to about 87%. The pH is again adjusted by adding a solution of acid, e.g., citric acid, to bring the pH into the gelling range of pectin. A second mixture is then prepared by hydrating the gelatin and adding glycerin, flavor and fruit. This mixture may be prepared at room temperature. The second mixture is added to the first mixture while the first mixture is still hot, e.g., at a temperature above about 80° C. Mixing is continued until uniformity is achieved. Finally, the aggregate (locust bean/carboxymethyl cellulose) is mixed in. The final mixture is then deposited, slabbed, extruded or otherwise shaped and formed and allowed to cool.

The resultant product is a chewy fruit flavored gel containing a high percentage of fiber. The product is substantially free from fibrous mouthfeel and is organoleptically pleasing.

Conventional soft and hard confections may also be employed as matricea. The preparation of soft confections, such as nougat, involves conventional methods, such as the combination of two primary components, namely (1) a high boiling syrup such as corn syrup or the like and (2) a relatively light textured frappe, generally prepared from gelatin, egg albumen, milk proteins such as casein and vegetable proteins such as soy protein, and the like. The frappe is generally relatively light, and may, for example, range in density from about 0.5 to about 0.7.

The high boiled syrup of the soft confectionery is relatively viscous and possesses a higher density, and frequently contains a substantial amount of sugar. Conventionally, the final nougat composition is prepared by the addition of a high boiled syrup to the frappe under agitation, to form the basic nougat mixture. Further ingredients such as flavoring, additional sugar, colorants, preservatives, medicaments, mixtures thereof and the like may be added thereafter also under agitation. A general discussion of the composition and preparation of nougat confections may be found in B. W. Minifie, *Chocolate, Cocoa and Confectionery Science and Technology*, 2nd Edition, AVI Publishing Co., Inc., Westport, Conn. (1980), at pages 424–425.

The procedure for preparing the "soft" confectionery involves known procedures. In general, the frappe component is prepared first and thereafter the syrup component is slowly added under agitation at a temperature of at least 65° C., and preferably at least 100° C. The mixing of components is continued to form a uniform mixture, after which the mixture is cooled to a temperature below 80° C., at which point the flavor may be added. The mixture is further mixed for an additional period until it is ready to be removed and formed into suitable confectionery shapes.

Similar to the soft confectionery, hard confectionery may be utilized in this invention. Likewise, it may be processed and formulated by conventional means. In general, a hard confectionery has a base composed of a mixture of cane or beet sugar, polyhydric alcohols and glucose syrup, low moisture levels, e.g., from 0.5 to 1.5% and are present in the final confectionery in amounts of between about 5% and about 99% by weight of the final composition. Such confectionery may be routinely prepared by conventional methods, such as those involving fire cookers, vacuum cookers and scraped-surface cookers also referred to as high speed atmospheric cookers.

Fire cookers involving the traditional method of making candy base, may be used. In this method the desired quantity of sugar is dissolved in water by heating in a kettle until the sugar dissolves. Corn syrup or an invert sugar is then added and cooking continued until a final temperature of 145° to 156° C. is achieved. The batch is then cooled and worked as a plastic-like mass to incorporate additives.

A high-speed atmospheric cooker uses a heat-exchange surface. Processes using it involve spreading a film of candy on a heat exchange surface, and heating the candy to 165° to 170° C. in a few minutes. The candy is then rapidly cooked to 100° to 120° C. and worked as a plasticlike mass enabling incorporation or the additives, such as flavor, color, acidulents and medicaments. It is at this point that the inventive aggreqates are blended into the candy in amounts of about 3 to about 20%.

In vacuum cookers, the sugar and corn syrup are boiled to 125° to 132° C. and vacuum applied and additional water is boiled off without extra heating. When cooking is complete, the mass is a semi-solid, having a plastic-like consistency. At this point, color, flavors and other additives are mixed in the mass by routine mechanical mixing operations.

The optimum mixing required to uniformly mix the flavor, color and other additives during conventional manufacturing of hard confectionery is determined by the time needed to obtain a uniform distribution of the materials. Normally, mixing times of 4 to 10 minutes have been found acceptable.

Once the candy mass has been properly tempered, it may be cut into workable portions or formed into desired shapes. A general discussion of the composition and preparation of hard confections may be found in H. A. Lieberman, *Pharmaceutical Dosage Forms: Tablets vol 1* (1980), Marcel Dekker, Inc. at pages 339 to 469.

It should be mentioned that the apparatuses useful in accordance with the present invention comprises those cooking and mixing apparatuses well known in the confectionery manufacturing arts, and therefore the selection of a specific apparatus will be apparent to the artisan.

The confectioneries useful in the delivery systems of this invention include, but are not limited to, sugarless boiled candy, lozenges, pressed tablets, toffee and nougat, gels, mints, syrups, liquids, elixirs and the like.

Flavors which may optionally be added to the delivery system are those well known in the confectionery art. For example, synthetic flavor oils, and/or oils derived from plants, leaves, flowers, fruits and so forth, and combinations thereof are useful.

Representative flavor oils include spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth.

The amount of flavoring agent employed is normally a matter of preference subject to such factors as flavor type, base type and strength desired. In general, amounts of about 0.05% to about 5.0% by weight of the final product are useful with amount of about 0.3% to about 1.5% being preferred and about 0.8% to about 1.2% being most preferred.

The edible matrix generally contains a sweetening agent. Sweetening agents may be selected from a wide range of materials such as water-soluble sweetening agents, water-soluble artificial sweeteners, and dipeptide based sweeteners, including mixtures thereof. Without being limited to particular sweetners, representative illustrations encompass:

A. Water soluble sweetening agents such ae monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium or calcium saccharin salts, cyclamate salts, acesulfam-K and the like, and the free acid form of saccharin.

C. Dipeptide based sweeteners such as L-aspartyl L-phenylalanine methyl ester and materials described in U.S. Pat. No. 3,492,131 and the like.

In general, the amount of sweetener will vary with the desired amount of sweetener selected for a particular matrix. The amount will normally be about 0.01% to about 90% by weight when using an easily extractable sweetener. The water-soluble sweeteners described in category A are preferably used in amounts of about 25% to about 75% by weight, and most preferably about 50% to about 65% by eight of the final delivery system. In contrast, the artificial sweetners described in categories B and C are used In amounts of about 0.005% to about 5.0% and most preferably about 0.05% to about 2.5% by weight of the final delivery system. These amounts are necessary to achieve a desired level of sweetness independent from the flavor level achieved from the flavor oil.

The edible matrix of this invention may likewise contain additional conventional additives, including fillers and mineral adjuvants such as calcium carbonate, magnesium carbonate and talc; emulsifiers such as glyceryl monostearate and lecithin; coloring agents such as titanium dioxide: fats and oils such as partially hydrogenated palm kernel oil and coconut oil; starches such as modified corn starch and tapioca dextrin as well as other conventional confectionery additives well known in the confectionery art.

The aggregates and delivery systems of the invention can be ingested "as is." That is, excipients and and other conventional additives for the active compound need not be used.

While delivery systems based on the instant invention are generally solid or semi-solid, it is contemplated that they may be employed, with or without the conventional supplemental agents, as principal components of systems to be dissolved or swallowed in water or other ingestible liquids for ingestion in a drinkable form.

Figure 1:
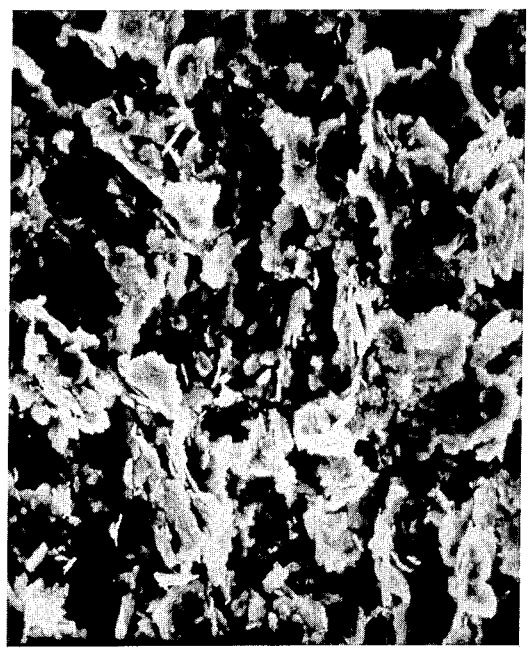
FIG. 1 is a photograph with 900x magnification of particles of locust bean gum.
Figure 2:
FIG. 2 is a photograph with 990x magnification of the inventive aggregates of locust bean gum and carboxymethyl cellulose. The difference in the size and shape of the aggregate particles as compared to the individual particles of FIG. 1 is apparent.
Figure 3:
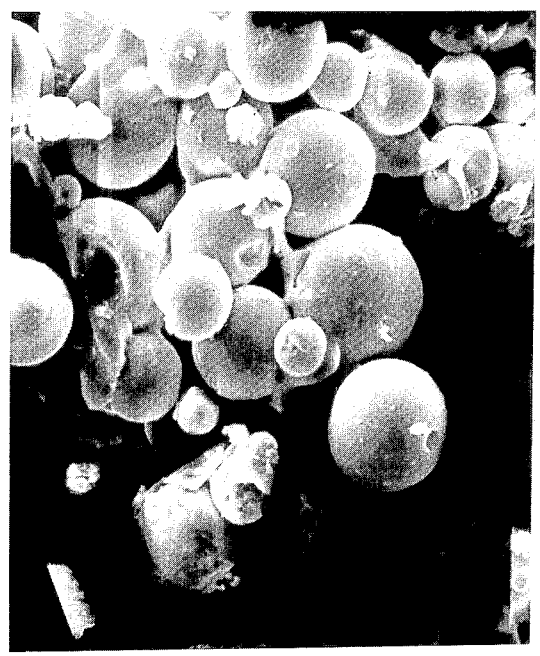
FIG. 3 is a magnified (300x) photograph of the coacervate particles made in accordance with Example I of the prior art U.S. Pat. No. 3,974,272. The spherical shapes are cholestyramine particles. The material between the cholestyramine is carboxymethyl cellulose.
Figure 4:
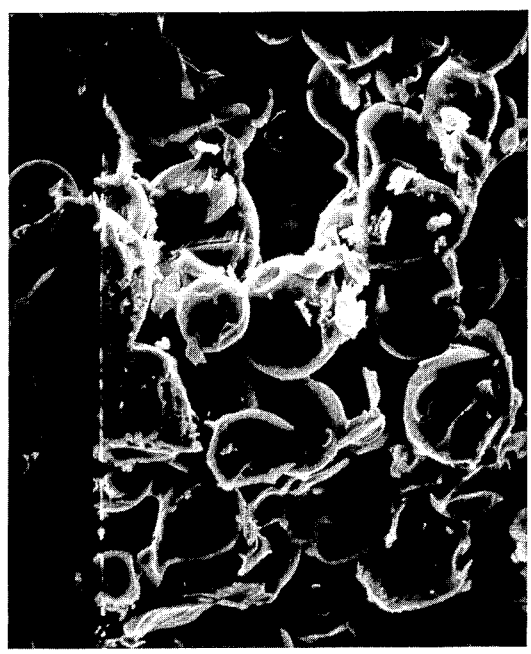
FIG. 4 is a magnified (300x) photograph of the inventive aggregate prepared in accordance with Example Three (cholestyramine and locust bean gum). The spherical spherical shapes are cholestyramine particles. The material surrounding and binding the cholestyramine particles is locust bean gum. The spherical cholestyramine particles are not as closely packed as in FIG. III (prior art) and it is apparent that more surface area of cholestyramine is available per unit weight.

The following examples are given to illustrate the invention, but are not to be limiting thereof. All percentages given throughout the specification are based upon weight unless otherwise indicated. Pressures are given in bars unless otherwise specified. A bar is a CGS unit equal to one dyne per centimeter squared, or 750 mm of mercury.

EXAMPLE 1

The example demonstrates the preferred aggregate and method of preparation. A mixture of 175.0 grams locust bean gum, 17.5 g. microcrystalline cellulose, 22.7 g. citric acid, 1.6 g. L-aspartyl-L-phenylalanine methylester, 1.6 g. sodium saccharin and 0.8 g. artificial colors was prepared. After dry blending, the mixture was air fluidized in a fluidized bed granulator. A 1.5% carboxymethyl cellulose aqueous solution was sprayed onto the fluidized mixture through a high pressure nozzle. The rate of spray is about 10 milliliters per minute using a preseure of about 2 bar. The particulate mixture is maintained in the fluidized state and sprayed intermittently. Drying is achieved after each spray cycle by the fluidizing air stream. This spray/dry cycle is continued until a bulk density of about 0.25 of the agglomerated particles is achieved. The bulk density was reached when the particle size had reached about 70 U.S. standard mesh. Upon reaching the desired bulk density particle size, the particles were dried in air at about 80° C. About 4.2 grams of flavoring was mixed into the particles. A Uniglatt fluidized bed granulator apparatus was used for the process. The rate of air flow was maintained at a level to allow for large agglomerates to form.

The resultant product was an ingestible aggregate comprising pre-swelled substantially anhydrous hydrocolloid (carboxymethylcellulose) and a dietary fiber (locust bean gum) whereby the hydrocolloid at least partially entraps and binds the dietary fiber. When 4.5 grams of the aggregate is mixed in 8 ounces of water, it was judged by a panel of experts to be a pleasant tasting fibercontaining liquid without the fibrous mouthful of the commercially available fiber-containing beverage mixes.

EXAMPLE 2

This example demonstrates the use of the inventive ingestible aggregates without any confectionery additives. Ground locust bean gum (about 270-400 mesh) in the amount of about 175 grams was fluidized in an air stream using a Uniglatt fluidized bed granulator. The particles of locust bean gum are then sprayed intermittently with a 1.5% aqueous solution of carboxymethyl cellulose. Spraying of the particles resulted in agglomeration and partial entrapment of the locust bean gum particles with the carboxymethyl cellulose. Drying of the particle was achieved between spray cycles by continuing the fluidizing air stream. The air stream flow rate was maintained at a speed which allowed for aggregate particles to be obtained having a mesh size of about 10 to about 70. The aggregate particles were found to be readily dispersible in water and lacked any fibrous mouthful. When sprinkled directly into food or eaten directly, the aggregate was judged by an expert panel to effectively mask the gritty, sandy taste common to dietary fiber.

EXAMPLE 3

A procedure similar to that used in Example 1 is used for the preparation of cholestyramine resin aggregates. Hydrated cholestyramine resin (25% solids) in the amount of about 400 grams was placed in a fluidized bed coater/granulator and was air dried until substantially anhydrous at a temperature of about 80°-100° C. The dried cholestyramine was removed from the granulator and mixed with fluid soybean lecithin to form a first mixture. Mixing continued until the cholestyramine resin was uniformly coated with the lecithin. About 240 milliliters of a 10% aqueous solution of acacia gum is sprayed onto the cholestyramine resin/lecithin mixture in a fluidized bed granulator in the manner of Examples 1 and 2. The rate of spray in about 10 milliliters per minute at a pressure of about 2 bar. The fluidized cholestyramine particles are intermittently sprayed while they are in the fluidized state. Drying of the thus formed aggregates is achieved between sprayings due to the circulating air. Each spraying tends to increase the aggregate particle size. As above, the air flow rate is regulated to obtain the desired aggregate particle size. A particle size of about 60-80 mesh is reached through alternative spraying and drying.

EXAMPLE 4

The fiber granules prepared as in Example 1 can be included in a gel-like confectionery type dosage vehicle. About 17.32 grams of citric acid and 19.04 grams of sodium citrate were dissolved in 950 grams of water. To this was added 57.26 grame standard 150 grade slow-set pectin, 1254 grams sucrose, and 100 grams corn syrup solids (24 D.G.). This mixture is boiled to achieve about 84% solids. To this first mixture is added an aqueous solution (200 grams water) containing 40 grams of granular gelatin, 50 grams of glycerin, 60 grams of dehydrated apples, 70 grams of dehydrated cranberries, and 2.5 grams of flavor. These mixtures are blended until the two are uniformly dispersed in each other. About 8.66 grams of citric acid dissolved in 11.88 grams of water is added and mixed until a uniform mixture is achieved. The resultant material comprises a gel-type confectionery matrix.

To this gel formulation is added 240 grams of the dietary fiber/hydrocolloid aggregate particles prepared as described in Example 1. The gel is formed and cut into convenient other dosage forms, e.g., bars or squares. Each dosage form contained about 5 to about 10 grams of fiber per 40 grams piece. The resultant product was judged by an expert panel to be devoid of the fibrous mouthfeel commonly associated with fiber.

EXAMPLE 5

The procedure of Example 4 was repeated using 240 grams of treated cholestyramine reain/hydrocolloid aggregates as prepared in Example 2 place of the fiber/hydrocolloid aggregates. The gel was formed and cut into convenient other dosage forms, each containing about 4 to about 6 grams of cholestyramine per 40 gram dosage form. The product was tested by an expert panel and was judged to be substantially free of the gritty, unpleasant mouthfeel commonly found in cholestyramine products.

EXAMPLE 6

The fiber/hydrocolloid aggregate particles were prepared as in Example 1 and incorporatad in a hard boiled candy dosage vehicle. About 52.16% (500 grams) of sucrose, and 34.72% (416 grams) of 42 DE corn syrup were dissolved in 300 grams of water. The solution was heated to about 150° C. to obtain a residual of moisture content of about 2.69%. About 10.43% (100 grams) of the aggregate particles of Example 1 were added to the molten candy base as it was cooling and mixed until uniformly dispersed. While the mixture was still in the fluid state, individual pieces were formed by passing the mass through drop rollers and allowing them to cool and harden.

The fiber-containing hard candy was then tasted by a panel of experts and was found to be pleasant tasting and void of the fibrous, gritty mouthful associated with fiber.

EXAMPLE 7

The fiber hydrocolloid aggregate particles prepared as in Example 1 were incorporated in a chocolate-tasting confectionery dosage vehicle. About 90% (450 grams) of the confectionery coating composition ingredients listed below were mixed and heated in a water bath until a temperature of about 50° C. was reached. About 10% (50 grams) of the aggregate particles were added to the melted coating and mixed until uniformly dispersed. The material was shaped into candy bars and allowed to solidify at room temperature. The resultant candy bars did not exhibit the gritty, fibrous taste but closely resembled a conventional chocolate-tasting bar.

Confectionery Coating Composition

| Confectionery Coating Composition | |
|---|---|
| Ingredient | % by Weight |
| Fractionated Vegetable Fat | 40 |
| Whole Milk Powder | 10 |
| Skim Milk Powder | 5.6 |
| Sugar | 44 |
| Cocoa | 0.17 |
| Salt | 0.2 |
| Vanillin | 0.03 |

EXAMPLE 8

This example demonstrates a delivery system having chewy candy or nougat-type of edible matrix containing the aggregate. The following formulation was used

| Ingredient | % by weight |
|---|---|
| Sugar (sucrose) | 39.5 |
| Corn syrup 42 DE | 26.3 |
| Water | 3.46 |
| Hydrolyzed milk protein | 0.37 |
| Water | 1.71 |
| Gelatin | 0.27 |
| Starch | 0.64 |
| Sorbitol ($\beta$-Crystalline) | 2.80 |
| Glycerin | 2.89 |
| Color | 0.01 |
| Acid (Citric) | 0.66 |
| Flavor | 0.30 |
| Lecithin | 4.34 |
| Partially hydrogenated vegetable oil | 3.86 |
| *Cholestyramine aggregates | 12.89 |

*Prepared as in Example 3.

In Preparing the delivery system the sugar and corn syrup were dissolved in water and heated at about 140° C. to obtain a candy base with 95% solids content. Hydrolyzed milk protein, water, gelatin, starch and sorbitol are combined in a separate mixture and whipped until an aerated foam is produced. The foam and the candy base are then mixed together with glycerin, color and acid. The inventive aggregates are then combined separately with lecithin and fluid vegetable oil. This mixture is then added to the candy-foam and mixed until uniform or homogenous. At this point, flavors are added and the entire mixture is fully cooled and formed into pieces. The resultant product was judged by an expert panel to be substantially free of the gritty mouthfeel commonly associated with cholestyramine products.

EXAMPLE 9

This example is intended to distinguish the inventive choleatyramine aggregates of Example 3 from Example 1 of the prior art coacervate disclosed in U.S. Pat. No. 3,974,272, previously discussed above.

The coacervate is a neutral complex of the anionic hydrocolloid and the Cationic cholestyramine. The inventive aggregates are a physical combination of dissociated ionic materials. If an ionio species such as sodium lauryl sulfate (SLS) is added to the coacervate solution, little or no reaction would he expected since no free ions from the coacervate would be available The inventive aggregate should, however, react extensively with the SLS, as the aggregate contains dissociated ionic species.

The following standard alkaline methylene blue two-phase titration test (*Systematic Analysis of Surface-Active Agents,* 2nd Ed., Rosen, M. J., and Goldsmith, H. A., Vol. 12, p429–430, John Wiley & Sons, Inc., 1972) was performed to demonstrate the above statements.

Reagents

Methylene blue solution—formed by dissolving 0.03 grams of methylene blue in 50 ml of water, mixing in 6.6 ml 96% $H_2SO_4$ and adding and dissolving 20.0 grams $Na_2SO_4$. Water is added to make 1 liter.

Hyamine 1622 (cationic surfactant) solution—formed by dissolving 1.814 grams of Hyamine 1622 (diisobutylphenoxyethoxydimethylbenzylammonium chloride, Rohm & Haas) in 1 liter of water to give a 0.004 N solution.

Procedure

Sodium lauryl sulfate (SLS anionic surfactant) in the amount of 4.1 grams was added to water to make a total volume of 250 ml. Ten (10) ml of this solution was pipetted into a 100-ml glass-stoppered graduated cylinder containing 15 ml $CHCl_3$ and 25 ml methylene blue solution. The cylinder was then shaken vigorously. The solution was titrated with Hyamine solution. The $CHCl_3$ layer is at first dark blue. At the endpoint, the blue color is less intense and equally dispersed between the aqueous and the chloroform layer.

Calculation $$\% \text{ anionic } (SLS) \text{ in aliquot} = \frac{H \times N_H \text{meq.} \times 100}{W^1}$$

in which H=ml Hyamine 1622: $N_H$=normality of Hyamine solution; meq=milliequivalent weight of anionic (SLS); and $$W^1 = \frac{\text{ml in aliquot} \times \text{sample weight}}{\text{solution volume}}$$

Results

|  | Inventive Aggregate Solution | Prior Art Coacervate Solution |
| --- | --- | --- |
| % unreacted SLS | 1.84 | 0.92 |

Conclusion

It is apparent that the inventive aggregates are quite different in character than the prior art coacervate as demonstrated by their respective reactivities with SLS. The inventive aggregates were significantly more reactive with SLS than the coacervate, as indicated by the lesser amount of unreacted SLS shown above. It is clear that the aggregates are not a neutral ionic complex as are the coacervates.

The invention being thus described, it will be obvious that the same may be varied in many ways. Such variations are not to be regarded as a departure from the spirit and scope of the invention and all such modifications are intended to be included within the scope of the following claims.

We claim:

1. A method for treating hypercholesterolemia and related disorders comprising administering to a patient in need of treatment of said condition a therapeutically effective amount of an ingestible aggregate composition comprising the aggregate particles produced by (a) preparing an aqueous composition of a hydrocolloid; (b) fluidizing substantially anhydrous substrate particles in an air stream; (c) contacting the substrate particle with the aqueous hydrocolloid composition to form the aggregates of the substrate and hydrocolloid; and (d) drying and collecting the aggregates, wherein the substrate contains cholestyramine.

2. A method for treating hypercholesterolemia and related disorders comprising administering to a patient in need of treatment of said condition a therapeutically effective amount of a delivery system comprising an edible matrix and an ingestible aggregate consisting essentially of a pre-swelled substantially anhydrous hydrocolloid and a substrate, wherein the hydrocolloid at least partially entraps and binds the substrate, the substrate being selected from the group consisting of dietary fibers, drugs and mixtures thereof, wherein the substrate and the hydrocolloid are not the identical material and wherein the substrate contains cholestyramine.

3. The method of claim 2 wherein the ratio of hydrocolloid to substrate is about 3:1 to about 20:1.

4. The method of claim 2 wherein the edible matrix is a confectionary composition.

5. The method of claim 4 wherein the edible matrix is present in amounts of about 50% to about 99.9% by weight of the delivery system.

6. The method of claim 2 wherein the hydrocolloid is selected from the group consisting of natural and modified gums, pectin mucillages, modified starches, noncellulosic polysaccharides, algal polysaccharides and mixtures thereof.

7. The method of claim 2 wherein the hydrocolloid is selected from the group consisting of carboxymethyl cellulose, methyl cellulose, karaya gum, sodium alginate, calcium alginate, and mixtures thereof.

8. A method of treating mineral deficiencies comprising administering to a patient in need of treatment of said condition a therapeutically effective amount of an ingestible aggregate composition comprising aggregate particles, produced by (a) preparing an aqueous composition of a hydrocolloid; (b) fluidizing substantially anhydrous substrate particles in an air stream; (c) contacting the substrate particles with the aqueous hydrocolloid composition to form the aggregates of the substrate and hydrocolloid; and (d) drying and collecting the aggregates, of a drug and a hydrocolloid wherein the hydrocolloid at least partially entraps the drug, and wherein the substrate is at least one drug selected from the group consisting of pharmaceutically acceptable salts of alkali metal and alkaline earth metals.

9. The method of claim 8 wherein the salt is selected from the group consisting of potassium chloride, calcium carbonate, magnesium oxide and mixture thereof.

* * * * *